United States Patent [19]

Taninaka et al.

[11] 4,080,467
[45] Mar. 21, 1978

[54] PHARMACEUTICAL COMPOSITIONS COMPRISING 1,3-DITHIOLAN-2-YLIDENE MALONATE DERIVATIVES

[75] Inventors: Kuniaki Taninaka, Ibaragi; Hitoshi Kurono, Amagasaki; Tsutomu Kasai, Sakai, all of Japan

[73] Assignee: Nihon Nohyaku Co., Ltd., Tokyo, Japan

[21] Appl. No.: 761,163

[22] Filed: Jan. 21, 1977

Related U.S. Application Data

[63] Continuation-in-part of Ser. No. 584,411, Jun. 6, 1975, abandoned.

[30] Foreign Application Priority Data

May 28, 1976 Japan .................................. 51-61914

[51] Int. Cl.² ............................................. A61K 37/00
[52] U.S. Cl. .................................................... 424/277
[58] Field of Search ......................................... 424/277

[56] References Cited

U.S. PATENT DOCUMENTS 3,761,596  9/1973  Taninaka et al. .................... 424/277

Primary Examiner—Frederick E. Waddell
Attorney, Agent, or Firm—Karl W. Flocks

[57] ABSTRACT

A 1,3-dithiolan-2-ylidene malonate derivative having the formula,

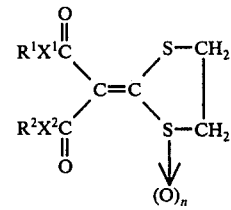

wherein $R^1$ and $R^2$, which may be the same or different, represent individually a $C_1$–$C_5$ alkyl group or a $C_1$–$C_4$ alkoxy-ethyl group; $X^1$ and $X^2$, which may be the same or different, represent individually an oxygen or sulfur atom; and n represents 0 or 1, is low in toxicity, has effects of stimulating, improving and recovering the functions of livers, and can prevent, alleviate and cure various liver damages of humans and animals when administered thereto either orally or parenterally.

28 Claims, No Drawings

PHARMACEUTICAL COMPOSITIONS COMPRISING 1,3-DITHIOLAN-2-YLIDENE MALONATE DERIVATIVES

The present application is a continuation-in-part of our copending application Ser. No. 584,411 filed June 6, 1975, now abandoned.

This invention relates to a process for controlling the liver damages of humans and animals, and to a pharmaceutical composition for use in said process.

More particularly, the invention is concerned with a pharmaceutical composition containing an effective amount of a compound having the general formula (I),

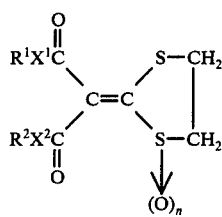

wherein $R^1$ and $R^2$, which may be the same or different, represent individually a $C_1$-$C_5$ alkyl group or a $C_1$-$C_4$ alkoxy-ethyl group; $X^1$ and $X^2$, which may be the same or different, represent individually an oxygen or sulfur atom; and $n$ represents 0 or 1.

The invention further relates to a pharmaceutical composition in the form of administration unit which contains a compound of the above-mentioned general formula (I) as active ingredient, either alone or in admixture with a pharmaceutically acceptable diluent.

The invention further pertains to a process for controlling the liver damages of humans and animals which comprises administering to the humans or animals a pharmaceutical composition in the form of administration unit which contains a compound of the above-mentioned general formula (I) as active ingredient, either alone or in admixture with a pharmaceutically acceptable diluent.

The term "controlling the liver damages" or the like, referred to in the body and the claims, means to prevent, alleviate or cure the liver damages.

In view of its various functions, the liver is frequently called a delicate chemical factory. Thus, in the liver, various chemical reactions are being biochemically effected, such as detoxication, sugar metabolism, protein metabolism, lipid metabolism, formation and secretion of bile, control of hormones, formation of blood coagulant prothrombin, regeneration of liver cells, and storage of various living body-constituting elements (fats, glycogens, proteins and vitamins).

However, even such delicate and well-balanced functions of the liver sometimes undergo damages, either acutely or chronically, due to various factors such as alcohols, insufficient nutrition, viruses, chemicals, toxicants, etc. to cause such diseases as, for example, hepatitis, liver necrosis, fatty liver, hepatocirrhosis and cholestasis.

As the result of extensive studies, the present inventors have found that compounds represented by the aforesaid general formula (I) have actions to activate liver cells and to activate various metabolic functions of the liver, such as sugar metabolism, detoxication, formation and excretion of bile flow and biliary salts (choleretic action), and hence can improve the damaged liver functions to provide such pharmacological effects as to alleviate or cure the damages and to protect the liver functions from certain damages.

An object of the present invention is to provide a novel pharmaceutical composition usable for controlling the liver damages of humans and animals.

Another object of the invention is to provide a process for controlling the liver damages of humans and animals.

Other objects and advantages of the invention will become apparent from the following description.

The compounds represented by the aforesaid general formula (I) partly include known compounds, and can be synthesized according to the following reaction scheme:

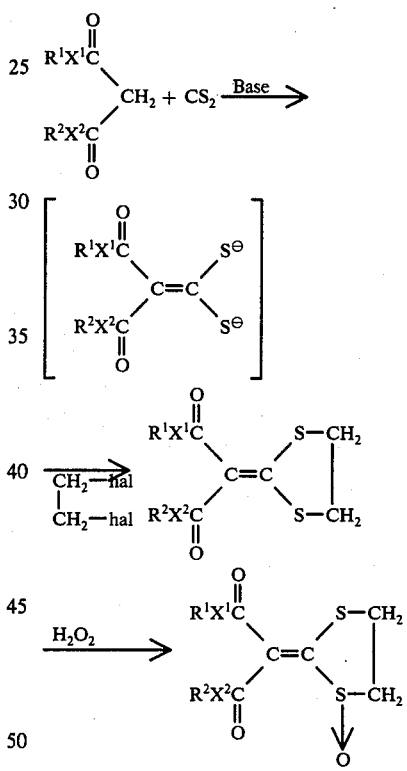

wherein $R^1$, $X^1$, $R^2$ and $X^2$ are as defined previously; and hal represents a halogen atom.

That is, a malonic or thiolmalonic acid ester is reacted with carbon disulfide in the presence of a base, and then the resulting dithiolate is reacted with a dihalogenoethane to obtain 1,3-dithiolan-2-ylidene malonate or thiol-malonate which corresponds to the compound of the general formula (I) when $n = 0$. Further, when the thus obtained malonate or thiomalonate is subjected to oxidation reaction with a suitable oxidizing agent, e.g. hydrogen peroxide, there is obtained an oxide which corresponds to the compound of the general formula (I) when $n = 1$.

Typical examples of the compounds represented by the general formula (I) are as shown in Table 1.

Table 1

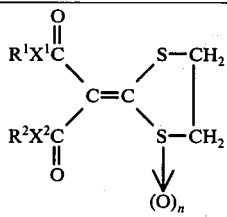

| No. | n | $X^1$ | $X^2$ | $R^1$ | $R^2$ | m.p. (° C) or b.p. (° C/mm Hg) or Refractive index |
|---|---|---|---|---|---|---|
| 1 | 0 | O | O | $CH_3$ | $CH_3$ | m.p. 64–66 |
| 2 | 0 | O | O | $C_2H_5$ | $C_2H_5$ | m.p. 48–49 |
| 3 | 0 | O | O | n-$C_3H_7$ | n-$C_3H_7$ | m.p. 50.5–51 |
| 4 | 0 | O | O | i-$C_3H_7$ | i-$C_3H_7$ | m.p. 54.5–55 |
| 5 | 0 | O | O | n-$C_4H_9$ | n-$C_4H_9$ | b.p. 171/0.09 |
| 6 | 0 | O | O | i-$C_4H_9$ | i-$C_4H_9$ | b.p. 177–183/0.25 |
| 7 | 0 | O | O | s-$C_4H_9$ | s-$C_4H_9$ | b.p. 175–180/0.5 |
| 8 | 0 | O | O | t-$C_4H_9$ | t-$C_4H_9$ | m.p. 88–89 |
| 9 | 0 | O | O | n-$C_5H_{11}$ | n-$C_5H_{11}$ | b.p. 192–194/0.07 |
| 10 | 0 | O | O | i-$C_5H_{11}$ | i-$C_5H_{11}$ | b.p. 180–186/0.08 |
| 11 | 0 | S | S | $CH_3$ | $CH_3$ | b.p. 134–138/0.1 |
| 12 | 0 | S | S | $C_2H_5$ | $C_2H_5$ | b.p. 132–135/0.1 |
| 13 | 0 | S | S | i-$C_3H_7$ | i-$C_3H_7$ | b.p. 151/1.5 |
| 14 | 0 | S | S | n-$C_4H_9$ | n-$C_4H_9$ | b.p. 148/0.07 |
| 15 | 0 | O | O | $CH_3OC_2H_4$ | $CH_3OC_2H_4$ | b.p. 204–205/0.09 |
| 16 | 0 | O | O | $C_2H_5OC_2H_4$ | $C_2H_5OC_2H_4$ | m.p. 36–38 |
| 17 | 0 | O | O | n-$C_4H_9OC_2H_4$ | n-$C_4H_9OC_2H_4$ | b.p. 208/0.06 |
| 18 | 0 | O | O | $CH_3$ | $C_2H_5$ | b.p. 158–159/0.15 |
| 19 | 0 | O | O | $CH_3$ | i-$C_3H_7$ | m.p. 67–68 |
| 20 | 0 | O | O | $CH_3$ | i-$C_4H_9$ | b.p. 173–175/0.05 |
| 21 | 0 | O | O | $C_2H_5$ | i-$C_3H_7$ | m.p. 51–52 |
| 22 | 0 | O | O | $C_2H_5$ | s-$C_4H_9$ | b.p. 171–173/0.2 |
| 23 | 0 | O | O | i-$C_3H_7$ | i-$C_4H_9$ | m.p. 47–49 |
| 24 | 0 | O | O | i-$C_3H_7$ | $C_2H_5OC_2H_4$ | m.p. 51–54 |
| 25 | 0 | O | O | $C_2H_5$ | $C_2H_5OC_2H_4$ | b.p. 171–175/0.07 |
| 26 | 0 | O | S | $C_2H_5$ | $C_2H_5$ | b.p. 172–174/0.7 |
| 27 | 0 | O | S | $C_2H_5$ | i-$C_3H_7$ | b.p. 170–179/0.7 |
| 28 | 0 | O | S | $C_2H_5$ | n-$C_4H_9$ | m.p. 31–32 |
| 29 | 1 | O | O | $CH_3$ | $CH_3$ | m.p. 49–54 |
| 30 | 1 | O | O | $C_2H_5$ | $C_2H_5$ | m.p. 75–77 |
| 31 | 1 | O | O | i-$C_3H_7$ | i-$C_3H_7$ | m.p. 78–83 |
| 32 | 1 | O | O | i-$C_4H_9$ | i-$C_4H_9$ | m.p. 66–72 |
| 33 | 1 | O | O | t-$C_4H_9$ | t-$C_4H_9$ | m.p. 129–134 |
| 34 | 1 | O | O | $CH_3$ | i-$C_4H_9$ | $n_D^{20}$ 1.5543 |
| 35 | 1 | O | O | $C_2H_5$ | i-$C_3H_7$ | m.p. 66–67 |
| 36 | 1 | O | O | i-$C_3H_7$ | $C_2H_5OC_2H_4$ | $n_D^{20}$ 1.5644 |

The compounds represented by the general formula (I) are extremely low in toxicity to mammals, and their acute oral toxicity to male mice expressed as $LD_{50}$ values are at such a low toxicity level as in the range from 1,000 to 6,000 mg/kg or more, in general. For example, the $LD_{50}$ values of the compounds 2, 4, 21 and 31 in Table 1 are 1,110 mg/kg, 1,350 mg/kgm, 2,230 mg/kg and more than 6,000 mg/kg, respectively. Further, these compounds have no detrimental effects on test animals administered therewith so far as the doses thereof are within an ordinary administration range.

The compounds of the general formula (I) are usable as pharmaceuticals for humans and animals. They have broad and various pharmaceutical spectra. The compound of the formula (I) has effects of stimulating, improving and recovering the functions of livers, and can prevent, alleviate or cure various liver damages of humans and animals when administered thereto either oraly or parenterally.

Experimental liver damages such as liver necrosis, hepatitis, fatty liver and hepatocirrhosis induced by administering chemicals such as carbon tetrachloride, chloroform, bromobenzene, dimethylnitrosoamine, thioacetamide, allyl alcohol, D-galactosamine or ethionine to animals, have been acknowledged as the models of human liver damages against which pharmaceuticals are sought.

Further, liver damages caused by toxic inorganic salts such as cadmium and selenium salts can be alleviated when they are administered.

They can show in animal tests such main effects as described below.

(1) The compounds of the present invention have effects of not only preventing all of the above experimental damages but also alleviating or curing the experimental hepatitis, fatty liver and hepatocirrhosis. Thus, they will be appreciated as pharmaceuticals usable for those purposes.

(2) They have actions to stimulate the alcohol metabolic function of the liver to lower the concentration of alcohol in the blood, and hence are effective for promotion of recovery from alcoholic intoxication and for prevention, alleviation and therapy of crapulence.

(3) They have actions to stimulate the sugar metabolic function of the liver to lower the abnormally elevated concentration of sugar in the blood, and hence are effective as blood sugar depressants and curatives for diabetes.

(4) They have action to stimulate the formation and the excretion of bile flow or biliary salts.

(5) When cadmium or selenium salts are administered to animals, which have previously been administered with the said compounds, the toxic symptoms caused by said salts are far more alleviated than in the case of blank animals.

Accordingly, the compounds represented by the general formula (I) are effective as preventives, alleviatives and curatives for liver damages, acute hepatitis, chronic hepatitis, fatty liver diseases, hepatocirrhosis, and chemical poisoning. Further, the said compounds are effective as depressants of alcohol in the blood, blood sugar depressants, diabetes curatives, cholestasis including the formation and the excretion of bile flow or biliary salts, and drugs for stimulating, promoting, improving and recovering metabolic functions of the livers.

In using the said compounds as the above-mentioned drugs, they may be formulated, according to usual procedures and means adopted in this field, into pharmaceutical compositions in the form of administration units convenient for their individual application purposes. That is, the said compounds are formulated into pharmaceutical compositions, either alone or in admixture with a pharmaceutically acceptable diluent, which may be any one of solids, semi-solids, liquids and intakable capsules, and are administered to humans or animals, either orally or parenterally.

Thus, the present invention provides a pharmaceutical composition which comprises the above-mentioned compound as active ingredient and, in admixture therewith, a pharmaceutically acceptble solid, semi-solid or liquid diluent.

The present invention further provides a pharmaceutical composition containing as active ingredient the above-mentioned compound in the form of a sterile and/or isotonic aqueous solution.

The present invention still further provides a pharmaceutical composition in the form of administration unit which contains the above-mentioned compound either alone or in admixture with a pharmaceutically acceptable diluent.

The pharmaceutical compositions of the present invention can be provided in such various administration unit forms as powders, granules, tablets, sugar-coated tablets, pills, capsules, suppositories, suspensions, liquids, emulsions, ampoules and injections.

The present invention includes such mode that the above-mentioned compound as active ingredient is administered singly. The present invention further includes such mode that the above-mentioned compound is administered in the form of a mixture with a pharmaceutically acceptable diluent. The diluent referred to herein means not only a mere diluent but also a pharmaceutically acceptable usual adjuvant. Examples of the mere diluent are those which are ordinarily used in the pharmaceutical field, and include such solid diluents as starch, lactose, calcium hydrogen phosphate, heavy magnesium oxide and the like, and such liquid diluents as water, isotonic solution, glucose solution and the like. Examples of the adjuvant include vehicles, extenders, binders, wetting agents, disintegrators, surfactants, lubricants, dispersants, buffer agents, seasonings, deodorants, dyes, flavors, preservatives and dissolution aids, though these are not limitative. These adjuvants may be used either singly or in the form of a mixture of two or more members.

The pharmaceutical composition of the present invention may be prepared according to any known method. For example, a mixture of the active ingredient and a diluent is formed, for example, into granules, and thus formed granular composition is molded, for example, into tablets. In case the pharmaceutical composition is for parenteral administration, it is preferable to be made aseptic and, if necessary, be made isotonic to the blood.

Generally, the pharmaceutical composition of the present invention contains about 0.01 to 100% by weight, based on the weight of the composition, of the active compound. Thus, the present invention includes such mode that the said compound is used independently.

The pharmaceutical composition of the present invention may be incorporated with other pharmaceutically active compound. In some cases, the composition may be incorporated with a plurality of the present compounds.

For the control of various liver damages and various diseases derived therefrom, the pharmaceutical composition of the present invention may be applied to humans and animals according to an ordinary procedure adopted in this field, in order to attain such effects as shown in the aforesaid animal tests. Thus, the composition of the present invention is administered orally or parenterally. The oral administration includes sublingual administration, and the parenteral administation includes administration by way of injection including, for example, subcutaneous, intramuscular and intravenous injections and instillation.

The dose of the pharmaceutical of this invention varies depending on many factors, including the kind of subject (whether the pharmaceutical is administered to humans or to animals), the difference in susceptibility, age, sex, body weight, the clinical picture, the physical conditions of patients, the means of administration, the time and interval of administration, the kind and properties of pharmaceutical composition, the kind of active ingredient, etc. In some cases, accordingly, the dose of the pharmaceutical may be made smaller than the minimum dose mentioned below, while in other cases the dose would be in excess of the maximum dose mentioned below. In case the pharmaceutical is to be administered in a large dose, it is preferable that the pharmaceutical is divisionally administered several times a day.

In the case of oral administration, effective dose for animals is in the range from 0.1 to 500 mg, preferably from 1 to 100 mg, of active ingredient per one kilogramme body weight per day. In the case of parenteral administration, effective dose for animals is in the range from 0.01 to 250 mg, preferably from 0.1 to 25 mg, of active ingredient per one kilogramme body weight per day.

In the case of oral administration, effective dose for humans, deduced from the above-mentioned effective dose for animals with consideration for susceptibility difference and security, is advantageously in the range from 0.1 to 250 mg, preferably from 0.5 to 50 mg, per one kilogramme body weight per day. In the case of parenteral administration, effective dose for humans is in the range from 0.01 to 100 mg, preferably from 0.1 to 25 mg, per one kilogramme body weight per day.

The present invention is illustrated in more detail below with reference to examples including a synthesis example, but the invention is not limited to the examples. In Examples 1 to 8, all parts are by weight.

SYNTHESIS EXAMPLE 1

Synthesis of di(methoxyethyl) 1,3-dithiolan-2-ylidene malonate

22 Grams (0.1 mole) of di(methoxyethyl) malonate and 7.6 grams (0.1 mole) of carbon disulfide were mixed. The mixture was cooled to 20° C, and was added dropwise with 40.2 g (0.3 mole) of 40% aqueous solution of caustic potassium while maintaining that temperature. After addition, the mixture was subjected to reaction at that temperature, added with 50 ml of water. Then 50 g (0.5 mole) of 1,2-dichloroethane was added thereto, and reacted at a temperature of 60° – 80° C for 4 hours. After completion of the reaction, the reaction mixture was subjected to extraction with 300 ml of ethyl ether. The extract was washed with water, dried, and subjected to distillation of ether.

A pale yellow oily substance having a boiling point of 204° – 205° C/0.09 mm Hg is obtained in an amount of 21.5 g (yield 68%) after distilling the residual under reduced pressure.

EXAMPLE 1

| | |
|---|---|
| Diethyl 1,3-dithiolan-2-ylidene malonate (Compound 2) | 10 parts |
| Heavy magnesium oxide | 10 parts |
| Lactose | 80 parts |

The above-mentioned components were homogeneously mixed and pulverized to obtain a powder.

EXAMPLE 2

| | |
|---|---|
| 2-(Diisopropoxycarbonyl)methyliden-1,3-dithiolan-1-oxide (Compound 31) | 10 parts |
| Synthetic aluminum silicate | 10 parts |
| Calcium hydrogenphosphate | 5 parts |
| Lactose | 75 parts |

The above-mentioned components were treated in the same manner as in Example 1 to obtain a powder.

EXAMPLE 3

| | |
|---|---|
| Diisopropyl 1,3-dithiolan-2-yliden malonate (Compound 4) | 50 parts |
| Starch | 10 parts |
| Lactose | 15 parts |
| Crystalline cellulose | 20 parts |
| Polyvinyl alcohol | 5 parts |
| Water | 30 parts |

The above-mentioned components were homogeneously kneaded, granulated, dried and sieved to obtain a granule.

EXAMPLE 4

99 Parts of the granule obtained in Example 3 was incorporated with 1 part of calcium stearate, and then subjected to compression molding to obtain a tablet of 10 mm. in diameter.

EXAMPLE 5

| | |
|---|---|
| Methyl isopropyl 1,3-dithiolan-2-ylidene malonate (Compound 19) | 95 parts |
| Polyvinyl alcohol | 5 parts |
| Water | 30 parts |

The above-mentioned components were treated in the same manner as in Example 3 to obtain a granule. 90 Parts of the thus obtained granule was incorporated within 10 parts of crystalline cellulose, and then subjected to compression molding to obtain a tablet of 8 mm. in diameter. Further, this tablet was formed into a sugar-coated tablet by use of proper amounts of a suspension comprising ethanolic shellac, syrup gelatin and precipitated calcium carbonate, and a dye.

EXAMPLE 6

| | |
|---|---|
| Ethyl isopropyl 1,3-dithiolan-2-ylidene malonate (Compound 21) | 4 parts |
| Nonionic surfactant | 10 parts |
| Isotonic sodium chloride solution | 86 parts |

The above-mentioned components were mixed together with heating to form a solution, which was then cooled to obtain an injection.

EXAMPLE 7

| | |
|---|---|
| Di-n-propyl 1,3-dithiolan-2-ylidene malonate (Compound 3) | 0.5 part |
| Nonionic surfactant | 2.5 parts |
| Distilled water for injection | 97 parts |

The above-mentioned components were treated in the same manner as in Example 6 to obtain an injection.

EXAMPLE 8

The powder obtained in Example 1 was filled into commercially available capsules to prepare a capsule.

EXAMPLE 9

Protective Effect on Acute Liver Damage associated with Centrilobular Necrosis (Experimental Model using Carbon Tetrachloride)

Carbon tetrachloride ($CCl_4$) administration induces centrilobular necrosis of the liver associated with loss of diphosphopyridine nucleotide, hepatic glycogen, coenzyme A and increase in neutral fat. Release of several enzymes from the hepatocytes, and increases of enzyme activities in the plasma are recognized as the result of the damage of the liver. A suitable means for evaluating the degree of damage induced by $CCl_4$ or the degree of protection afforded by drugs is to study the plasma glutamic-pyruvic transaminase (p-GPT) activity.

Method: The test compounds were dissolved or suspended in olive oil and administered orally at the dose of 250 mg/kg to the mice (Four-week-old male mice-dd strain). After 6 hours, $CCl_4$ was administered orally (0.05 ml/kg as olive oil solution). Animals were killed 24 hours after $CCl_4$ administration, and the liver was grossly observed. The plasma was obtained by centrifugation. Activities of p-GPT were determined by the method of Reitman and Frankel and expressed in Karmen units.

Score for liver damage was as follows:

| Liver damage index | Description |
|---|---|
| 0 | Normal |
| 2 | Slightly recognized |
| 4 | Clearly observable damage |
| 6 | Heavy damage |

Each figure indicates average of 5 to 6 mice. Values of p-GPT over 1,000 Karmen unit regarded as 1,000 for calculation of average for convenience.

Table 2

| | Result | |
|---|---|---|
| Compd. No. | Liver Damage Index | p-GPT |
| 1 | 2.2 | 200 |
| 2 | 0.8 | 47 |

Table 2-continued

| Compd. No. | Result Liver Damage Index | p-GPT |
|---|---|---|
| 3 | 1.0 | 26 |
| 4 | 0.2 | 23 |
| 5 | 3.0 | 322 |
| 6 | 0.5 | 26 |
| 7 | 1.2 | 102 |
| 8 | 1.2 | 230 |
| 9 | 3.2 | 550 |
| 10 | 3.3 | 350 |
| 11 | 2.5 | 750 |
| 12 | 1.0 | 36 |
| 13 | 1.4 | 105 |
| 14 | 1.4 | 241 |
| 15 | 1.5 | 85 |
| 16 | 1.0 | 150 |
| 17 | 3.0 | 242 |
| 18 | 1.4 | 240 |
| 19 | 1.0 | 89 |
| 20 | 0.2 | 62 |
| 21 | 0.6 | 64 |
| 22 | 0.4 | 67 |
| 23 | 1.0 | 102 |
| 24 | 1.2 | 152 |
| 25 | 1.0 | 85 |
| 26 | 0.6 | 62 |
| 27 | 0.4 | 18 |
| 28 | 0.8 | 31 |
| 29 | 0.6 | 222 |
| 30 | 0.8 | 156 |
| 31 | 0.8 | 121 |
| 32 | 1.0 | 180 |
| 33 | 1.4 | 212 |
| 34 | 1.0 | 102 |
| 35 | 0.8 | 152 |
| 36 | 1.4 | 210 |
| Carbon tetrachloride alone | 5.2 | >1,000 |
| Thioctic acid amide | 4.8 | 763 |
| Anethol trithion | 1.6 | 38 |
| Control | 0 | 35 |

Carbon tetrachloride is best suitable for bringing test animals to the state of acute hepatitis. As is clear from the results of tests carried out by use of carbon tetrachloride, all the active ingredients used in the present composition show prominent liver damage-preventing effects, and are comparable in effectiveness to thioctic acid amide and anethol trithion which are commercially available at present as liver drugs.

Accordingly, the compounds of this invention are useful as pharmaceutical for human and animal acute hepatitis.

EXAMPLE 10

Thereapeutic Effect on Chronic Liver Damage (Experimental Model Using Thioacetamide)

Thioacetamide (hereinafter abbreviated to "TAA") also causes liver damages in animals, like carbon tetrachloride, and hence is frequently used as a chemical for bringing about hepatitis and fatty liver diseases. In the tests of this Example, TAA was repeatedly administered to animals to prepare test animals suffering from somewhat chronic liver damages, and then the present compounds were administered thereto to know whether or not the compounds were effective against chronic hepatitis.

The degree of the liver damage and the therapeutic effects of the compounds were evaluated according to BSP test. The BSP test is a method in which BSP (sulfobromophthalein sodium), a dye known to be quickly metabolized in and excreted from the liver, is intravenously injected into animals and, after a definite period of time, the blood is taken out to measure the amount of BSP remaining in the plasma. In case the animals are suffering from the liver damage, the dye will remain, according to the degree of the damage, at the stage where a major portion of BSP is metabolized and excreted in the case of normal animals.

Five groups of rats (Sprague Dawley strain) were treated as follows:

Group A: The rats were orally administered with 100 mg/kg of thioacetamide, at 3 days intervals for 36 days (12 times of the administration), then were submitted for 10 days to a normal diet.

Group B: The rats were orally administered with 100 mg/kg of thioacetamide at 3 days intervals for 36 days (12 times of the administration), then were submitted for 10 days to the normal diet + 0.2% of compound 4.

Group C: The rats were orally administered with 100 mg/kg of thioacetamide at 3 days intervals for 36 days (12 times of the administration) then were submitted for 10 days to the normal diet + 0.2% of compound 2.

Group D: The rats were orally administered with 100 mg/kg of thioacetamide at 3 days intervals for 36 days (12 times of the administration) then were submitted for 10 days to the normal diet + 0.2% of anethol trithion.

Group E: The rats were submitted to the normal diet as the control.

Five rats were sacrified from each group at appropriate intervals for BSP (sulfobromophthalein) test, the results of which were shown as amounts (mg) of BSP remaining in 1 dl of plasma.

Table 3

| Time of sacrifice | Concentration of BSP in plasma (mg/dl) | | | | |
|---|---|---|---|---|---|
| | Group A | Group B | Group C | Group D | Group E |
| 24 hr after 4 times TAA administration | 18.2±2.6 | | | | 0.3±0.1 |
| 24 hr after 8 times TAA administration | 16.8±5.2 | | | | — |
| 24 hr after 12 times TAA administration | 17.3±4.4 | | | | 0.8±0.1 |
| After compounds administration | | | | | |
| 2 Days | 12.7±3.7 | 7.6±1.1 | 9.8±3.1 | 9.7±4.1 | 0.4±0.1 |
| 5 Days | 8.7±1.9 | 3.8±0.5 | 4.7±0.8 | 7.3±3.4 | — |
| 10 Days | 1.4±0.4 | 0.3±0.1 | 0.8±0.2 | 0.9±0.1 | 0.6±0.1 |

By the repeated administration of TAA. the concentration of BSP in the blood increased to 16 to 19 mg/dl and the said level lasted, and therefore it is considered that the rats were brought to a state close to chronic hepatitis. After the administration of TAA, the present compound-administered groups (Groups B and C) were quicker in cure of liver damage than the unadministered group (Group A). This indicates that the present compounds are effective against chronic hepatitis as well.

EXAMPLE 11

Protective Effect on Acute Liver Damage associated with Periportal Necrosis (Experimental Model using Allyl Alcohol)

Methods

The compound of this invention or anethol trithion was orally administered to the male mouse (4 week-old dd-strain) at the dose of 100 mg/kg. Six hours after it, allyl alcohol was orally administered at the dose of 0.075 ml/kg. Twenty four hours after it, the animals were sacrificed to collect blood samples. The residual quantity of BSP was measured by BSP test, from which the protective effect of the compound of this invention was evaluated.

Table 4
Results

Protective effect on acute liver damage associated with periportal necrosis

| Hepato-toxin | Index of hepato-toxicity | Control | Positive control* | Compound 4** | Anethol trithion** |
|---|---|---|---|---|---|
| Allyl alcohol | BSP | 1.8±0.4 | 28.4±4.8 | 16±2.3 | 19.3±4.6 |

*Hepatotoxin alone was administered.
**After treatment with Compound 4 or anethol trithion, the hepatotoxin was administered.

Allyl alcohol differs from carbon tetrachloride or bromobenzene, dimethylnitrosoamine or chloroform in that it induces liver damage associated with periportal necrosis. As shown in Table 4, the compound of this invention protected the liver damage.

Accordingly, the compound of this invention is useful as a pharmaceutical for human or animal liver disease accompanied with periportal necrosis.

EXAMPLE 12

Protective Effect on Acute Hepatitis associated with Mesenchymal Reaction and Discrete Lobular Necrosis (Experimental Model using D-Galactosamine)

D-Galactosamine is a compound which induces a discrete lobular necrosis associated with mesenchymal reaction similar to the change observed in human viral hepatitis, so that it is frequently used in producing a model for viral hepatitis.

Methods

The compound of this invention or anethol trithion was administered orally to the male rat (SD strain) at the dose of 100 mg/kg. Six hours after it, D-galacetosamine was intraperitoneally administered at the dose of 600 mg/kg. Four hours after it, an additional 300 mg/kg was administered intraperitoneally. Eight hours after it, the animals were sacrificed to collect the blood samples. P-GPT activity and triglyceride in the liver were measured to evaluate the effect of the compound of this invention.

Table 5
Results

Protective effect on acute liver damage associated with discrete lobular necrosis

| Hepatotoxin | Index of hepato-toxicity | Control | Positive control* | Compound 2** | Compound 4** | Compound 21** | Anethol tri-thion** |
|---|---|---|---|---|---|---|---|
| D-Galactos-amine | p-GPT (Karmen unit) | 13±0.5 | 92±59 | 68±32 | 63±23 | 47±21 | 106±30 |
| | Triglyce-ride in liver (mg/g) | 6.5±1.2 | 8.2±2.2 | 7.2±1.5 | 4.6±0.73 | 6.8±1.2 | 9.2±1.5 |

*The hepatotoxin alone was administered.
**After a treatment with Compound 2, Compound 4, Compound 21 or anethol trithion the hepatotoxin was administered.

As shown in Table 5, the compound of this invention protected the liver damage.

The compound of this invention, accordingly, is useful as a pharmaceutical for use in therapying human or animal hepatitis accompanied with mesenchymal reaction and discrete lobular necrosis.

EXAMPLE 13

Effect on Fatty Liver (Experimental Model using Ethionine)

There are known many factors inducing fatty liver. But, the fatty liver is grouped into a couple of patterns from the mechanism of lipid accumulation or metabolism of lipoprotein in the liver. Ethionine is a typical compound inducing fatty liver. It inhibits RNA and protein syntheses and destructs polysome of the liver cell. Fatty liver is induced by the inhibition of protein synthesis and the disturbance of lipoprotein secretion.

Usually, fatty liver is closely related to the accumulation of triglyceride in the liver. In the present example, the degree of fatty liver and protective or therapeutic effect against the fatty liver was evaluted by measurement of triglyceride content in the liver.

Methods

The animals used in the test were 4 week-old male mice (dd-strain).

The mice were submitted for 5 days to a normal diet (control), to the normal diet plus 0.2% ethionine (positive control), to the normal diet plus 0.2% ethionine and 0.2% of the compound of this invention, or to the normal diet plus 0.2% ethionine and 0.2% methionine which was the referential diet. At the end of the period of 5 days, content of triglyceride in the liver was studied colorimetrically by chromotropic acid method and the result was represented as triolein content (mg/g-liver).

Table 6

| Results Effect on fatty liver | |
|---|---|
| Group | Triglyceride (mg/g) |
| Control | 6.7 ± 0.72 |
| Ethionine + Compound 30 | 12.6 ± 2.3 |
| Ethionine + Compound 4 | 10.4 ± 1.6 |
| Ethionine + Compound 22 | 11.3 ± 0.96 |

Table 6-continued

Results
Effect on fatty liver

| Group | Triglyceride (mg/g) |
|---|---|
| Ethionine + Methionine | 13.2 ± 2.1 |
| Ethionine alone | 20.5 ± 1.6 |

The compounds of this invention depressed the abnormal accumulation of triglyceride in the liver, induced by ethionine, to exhibit a protective and therapeutic effect against fatty liver. The compounds of this invention were superior to methionine in the above-mentioned effect.

Accordingly, the compounds of this invention are useful as pharmaceutical for human and animal fatty liver.

EXAMPLE 14

Therapeutic Effect on Fatty Liver (Experimental Model using Carbon Tetrachloride)

Carbon tetrachloride also induces fatty liver, but the picture of disease differs from the case of ethionine-induced fatty liver. Carbon tetrachloride is generally considered to damage microsome and thereby to inhibit protein synthesis and induce fatty liver.

Methods

Carbon tetrachloride was subscutaneously administered to 35 week-old male rat (SD strain) for 4 days at the dose of 1 ml/kg. The treated animals were left for 3 days after the last administration to maximize the manifestation of fatty liver.

Administration of the compounds of this invention was commenced on the fourth day after the administration of carbon tetrachloride was completed. It was orally given everyday for 10 days at the dose of 50 or 250 mg/kg. On the 11th day, the animals were sacrificed. The therapeutic effect was evaluated by determining the content of lipid in the liver (triglyceride and total lipid) and examining the histopathological changes. Triglyceride and total lipid were determined colorimetrically by chromotropic acid method and Bragdon's oxidation method, respectively.

Indices for the histopathological change is as follows.

| Index | Histopathological changes |
|---|---|
| − | Normal |
| ± | Formation of small droplet deposition of lipid but the number of droplet is not so many. |
| + | formation of small or slightly fused droplet deposition of lipid and increasing the number of droplet |
| ++ | Formation of fused large droplet deposition of lipid |

Table 7

Results

Therapeutic effect on fatty liver

| Group | | Triglyceride (mg/g-liver) | Total lipid (mg/g-liver) |
|---|---|---|---|
| Control | | 12.3 ± 1.6 | 61.8 ± 5.8 |
| Positive control | | 62.3 ± 10.3 | 183.3 ± 28.6 |
| Compound 4 | (50 mg/kg) | 42.3 ± 6.3 | 107.6 ± 12.3 |
| ibid. | (250 mg/kg) | 23.6 ± 3.8 | 72.3 ± 9.6 |
| Compound 21 | (50 mg/kg) | 40.6 ± 6.8 | 97.8 ± 10.3 |
| ibid. | (250 mg/kg) | 24.8 ± 3.2 | 70.2 ± 8.3 |
| Compound 32 | (50 mg/kg) | 48.3 ± 7.6 | 112.4 ± 12.3 |
| ibid. | (250 mg/kg) | 26.3 ± 4.2 | 77.2 ± 8.7 |

Table 7-continued

Results

Therapeutic effect on fatty liver

| Group | | Triglyceride (mg/g-liver) | Total lipid (mg/g-liver) |
|---|---|---|---|
| Methionine | (250 mg/kg) | 58.2 ± 9.6 | 168.6 ± 21.6 |

Table 8

Therapeutic effect on fatty liver
(Histopathological examination)

| Group | | Degree of fatty liver | | | | | | |
|---|---|---|---|---|---|---|---|---|
| Control | | − | − | − | − | − | | |
| Positive control | | + | + | ++ | ++ | ++ | | |
| Compound 4 | (50 mg/kg) | ± | ± | ± | ± | ± | + | ± |
| ibid. | (250 mg/kg) | − | − | ± | ± | − | ± | − |
| Compound 13 | (50 mg/kg) | ± | ± | ± | ± | ± | + | ± |
| ibid. | (250 mg/kg) | − | ± | − | ± | ± | ± | − |
| Compound 6 | (50 mg/kg) | ± | ± | ± | ± | + | ± | ± |
| ibid. | (250 mg/kg) | ± | − | − | − | ± | ± | ± |
| Methionine | (250 mg/kg) | + | ± | ++ | ++ | ++ | ± | + |

As shown in Table 7, the group "Positive control" to which carbon tetrachloride was administered but thereafter the compound of this invention was not administered manifested a high degree of fatty liver and showed no sign of improvement.

On the other hand, in the therapeutic groups to which the compound of this invention was given at the dose of 50 or 250 mg/kg the degree of fatty liver was significantly improved. In other words, the compound of this invention exhibited a therapeutic effect.

On the contrary, methionine hardly exhibited a therapeutic effect against fatty liver induced by carbon tetrachloride.

Table 8 illustrates the results of histopathological examination. The size and number of lipid droplet decreased in the groups therapied with the compounds of this invention, demonstrating an alleviation of fatty liver.

Accordingly, the compound of this invention is useful as pharmaceutical for fatty liver in humans and animals.

EXAMPLE 15

Therapeutic Effect on Cirrhosis

Almost all the liver diseases induced by various causes are considered to advance, finally, to cirrhosis. The cirrhosis is a final stage of liver disease, which is difficult to classify from the causal viewpoint. Usually, experimental cirrhosis is induced by longterm repeated administration of carbon tetrachloride.

The therapeutic effect of the compound of this invention on cirrhosis, which had been caused by carbon tetrachloride administration, was examined.

Methods

A 10% solution of carbon tetrachloride in olive oil was administered to the male rat (4 week-old SD-strain) intraperitoneally at the dose of 0.5 ml carbon tetrachloride/kg twice a week for a period of 10 weeks, to induce cirrhosis. Four days after the final administration of carbon tetrachloride, the formation of pseudolobulus was confirmed. Then the diseased animals were divided into two groups. Therapeutic group was submitted a diet containing 2000 ppm of Compound 4, while the positive control group was submitted a normal diet. Control group, to which olive oil alone had been administered, was submitted a normal diet.

At 1, 2, 4 and 8 weeks after beginning of Compound 4 feeding, 5 animals from each group were sacrificed, and the therapeutic effect on cirrhosis was evaluated by examining plasma transaminase activity (p-GPT and p-GOT, Reitman-Frankel method) and observing histopathological changes.

Degree of cirrhosis in the histopathological examination was graded as follows:

| Index | Histopathological changes |
|---|---|
| − | Normal |
| ± | Slight formation of pseudo lobulus |
| + | Slight formation of pseudo lobulus, slight fibrosis |
| + + | Moderate formation and cohesion of pseudo lobulus, moderate fibrosis |
| + + + | Severe cohesion of pseudo-lobulus, severe fibrosis |

Table 9

Results

Therapeutic effect of the compound of this invention on cirrhosis (Transaminase activity)

| Period of therapy (week) | p-GPT activity (Karmen unit) | | | p-GOT activity (Karmen unit) | | |
|---|---|---|---|---|---|---|
| | Control | Positive control | Therapeutic group | Control | Positive control | Therapeutic group |
| 0 | 24.0±2.2 | 122±18 | | 62.8±5.1 | 491±83 | |
| 1 | 20.6±1.7 | 78.2±18.6 | 81.6±25.9 | 58.8±4.7 | 264.6±56 | 277±135 |
| 2 | 21.2±2.0 | 33.8±2.0 | 28.8±3.0 | 54.8±2.5 | 123±16 | 96.8±2.6 |
| 4 | 38.8±2.1 | 43.0±3.8 | 40.6±3.8 | 79.2±5.5 | 82.8±3.5 | 64.0±5.5 |
| 8 | 23.6±3.3 | 35.8±4.4 | 32.8±6.1 | 78.6±2.6 | 105.8±8.2 | 91.8±7.2 |

Table 10

Therapeutic effect of the compound of this invention on cirrhosis (Histopathological examination)

| Period of therapy (week) | Control | | | | | Positive control | | | | | Therapeutic group | | | | |
|---|---|---|---|---|---|---|---|---|---|---|---|---|---|---|---|
| 0 | − | − | − | − | − | ± | + | ++ | ++ | + | | | | | |
| 1 | | | | | | ++ | ++ | + | +++ | +++ | + | +++ | + | ++ | +++ |
| 2 | | | | | | ± | +++ | + | ++ | ± | ++ | ± | ± | ± | ± |
| 4 | | | | | | ++ | + | ++ | + | ++ | ± | ± | ± | ± | + |
| 8 | | | | | | +++ | ++ | ± | + | ++ | + | ± | +++ | ± | ± |

It was considered that all the animals had reached the stage of cirrhosis after carbon tetrachloride was administered for a period of ten weeks. As shown in Table 9, the compound normalized the elevated plasma transaminase activity, particularly plasma GOT activity, rapidly.

Table 10 illustrates the therapeutic effect on cirrhosis. In the positive control group, a moderate to high degree of cirrhosis including fibrosis of liver, appearance of pseudo-lobulus and its cohesion was observed over a period of 8 weeks after the final administration of carbon tetrachloride. On the contrary, in the therapeutic group the cohesion of pseudo-lobulus and the fibrosis were ameliorated after two weeks had passed, demonstrating the therapeutic effect of the compound on cirrhosis.

Thus, the compound in this invention is useful as pharmaceutical for therapying chronic liver diseases and cirrhosis in humans and animals.

EXAMPLE 16 — Cholagogic Action

Formation and excretion of biliary salts in the bile outflow are the important metabolic functions of the liver. If the bile flow is damaged by some cause, cholestasis and several types of liver diseases accompanying jaundice will be induced.

Drugs as choleresis are used for patients to improve bile flow. In the present example, the effect of the compound of the invention on the quantities of bile and biliary salt is investigated.

Methods

The male rat (4 week-aged, SD-JCL strain) was anesthetized with sodium pentobarbital (37.5 mg/kg, intraperitoneal injection). The abdominal cavity was opened through a midline incision. The common bile duct was catheterized with polyethylene tube o.d. 0.8 mm. The catheter was brought to the outside through the abdominal incision wound prior to closing. Bile was collected from the catheter continuously with time intervals of one hour. The quantity of bile produced in one hour was determined by weighing and that of biliary salt was determined by enzymatic method (Ikagaku Jikkenho Koza 1B, Biological Constituents II, edited by Tamio YAMAKAWA). The amount of biliary salts was represented as cholic acid equivalent.

In the representation of the results, the quantities of bile and biliary salts produced in one hour prior to the administration of drug were taken as 100. The compound of this invention was orally administered at the dose of 200 mg/kg. As reference anethol trithion was used.

Table 11

Results

Effect on bile flow

| | Experiment 1 | | Experiment 2 | | Experiment 3 | | Experiment 4 | |
|---|---|---|---|---|---|---|---|---|
| Time | Control | Compound 2 (200 mg/kg) | Control | Compound 4 (200 mg/kg) | Control | Compound 20 (200 mg/kg) | Control | Anethol trithion (200 mg/kg) |
| Before treat- | | | | | | | | |

Table 11-continued

Results
Effect on bile flow

| | Experiment 1 | | Experiment 2 | | Experiment 3 | | Experiment 4 | |
|---|---|---|---|---|---|---|---|---|
| Time | Control | Compound 2 (200 mg/kg) | Control | Compound 4 (200 mg/kg) | Control | Compound 20 (200 mg/kg) | Control | Anethol trithion (200 mg/kg) |
| ment 1 hour After treatment | 100 | 100 | 100 | 100 | 100 | 100 | 100 | 100 |
| 1 hour | 100±2.4 | 108±3.8 | 100±2.4 | 110±4.2 | 100±2.4 | 113±4.3 | 104±3.5 | 114±15 |
| 2 | 104±6.5 | 116±6.2 | 104±6.5 | 115±6.3 | 104±6.5 | 112±8.2 | 101±4.9 | 114±15 |
| 3 | 92±6.4 | 109±8.3 | 92±6.4 | 110±7.2 | 92±6.4 | 106±6.3 | 93±6.9 | 102±11 |
| 4 | 88±9.7 | 108±8.5 | 88±9.7 | 112±8.5 | 88±9.7 | 113±8.8 | 84±6.7 | 95±7.7 |
| 5 | 85±9.3 | 98±3.8 | 85±9.3 | 92±4.7 | 85±9.3 | 93±3.8 | 76±6.6 | 86±6.6 |

Table 12

| | Experiment 1 | | Experiment 2 | | Experiment 3 | | Experiment 4 | |
|---|---|---|---|---|---|---|---|---|
| | Effect on the excretion of biliary salt | | | | | | | |
| Time | Control | Compound 2 (200 mg/kg) | Control | Compound 4 (200 mg/kg) | Control | Compound 20 (200 mg/kg) | Control | Anethol trithion (200 mg/kg) |
| Before treatment 1 hour | 100 | 100 | 100 | 100 | 100 | 100 | 100 | 100 |
| After treatment | | | | | | | | |
| 1 hour | 89±6.6 | 108±18 | 89±6.6 | 105±13 | 89±6.6 | 104±11 | 94±6.2 | 108±12 |
| 2 | 92±11 | 120±12 | 92±11 | 125±20 | 92±11 | 119±13 | 89±9.5 | 89±11 |
| 3 | 66±8.8 | 133±18 | 66±8.8 | 132±26 | 66±8.8 | 120±17 | 77±11 | 66±3.8 |
| 4 | 54±15 | 120±21 | 54±15 | 115±23 | 54±15 | 113±18 | 56±9.7 | 47±3.0 |
| 5 | 46±16 | 86±8.9 | 46±16 | 81±7.2 | 46±16 | 82±7.3 | 52±10 | 3.3±4.0 |

As shown in Table 11, bile flow was elevated by the administration of the compound of this invention. Quantity of total excreted bile for 5 hours after administration of Compound 2, Compound 4 and Compound 20 was 1.15, 1.15 and 1.14 times, respectively, greater than that in control. In the case of anethol trithion the quantity of total excreted bile was 1.10 times greater than that in control.

As shown in Table 12, the amount of excreted biliary salts was remarkably increased by the administration of the compound of this invention. Amount of total biliary salts excreted for 5 hours after administration of Compound 2, Compound 4 and Compound 20 was 1.63, 1.61 and 1.55 times, respectively, greater than that in control. In the case of anethol trithion, however, no particular increase was observed in the excretion of biliary salts. In other words, the compounds of this invention were particularly effective in promoting the excretion of biliary salt.

The compound of this invention is to be classified as drug for increasing the excretion of biliary salts, namely cholanertica, and their effectiveness to diseases of human or animal liver or bile duct can readily be expected from the hitherto reported findings concerning the behavior of anethol trithion. As above, the compound of this invention can stimulate the metabolic function of the liver and therefore is useful as pharmaceutical for controlling liver diseases causes by cholestasis.

EXAMPLE 17

Effect on Concentration of Ethyl alcohol in the Blood

The test compounds are dissolved or suspended in olive oil and administered orally at the dose of 250 mg/kg to the mice. After 6 hours, 1,000 mg/kg of ethyl alcohol was given orally. Blood was taken in a capillary from caudal vein at the time indicated in the results. The plasma was obtained by centrifugation. The concentration of ethyl alcohol in the plasma was measured by FID type gas liquid chromatography. Five mice were used for each group.

Table 13

| | Result: Concentration of Ethyl alcohol in Plasma (ppm) | | | | |
|---|---|---|---|---|---|
| Time (min.) | Control | comp. Pre-treated | | | |
| | | Compd. 4 | Compd. 2 | Compd. 26 | Compd. 31 |
| 0 | 27±17 | 9±4 | 8±3 | 10±3 | 12±8 |
| 5 | 875±203 | 727±84 | 712±75 | 690±102 | 720±145 |
| 15 | 810±191 | 715±146 | 65±98 | 694±86 | 583±122 |
| 30 | 690±214 | 430±105 | 422±100 | 432±96 | 343±13 |
| 60 | 167±76 | 13±11 | 15±8 | 12±8 | 5±2 |
| 120 | 5±1 | Not detected | Not detected | Not detected | Not detected |

The concentration of ethyl alcohol in the plasma of the present compound-treated mice was lower than that of normal mice. This tendency was particularly marked at the stages of 30, 60 and 120 minutes after administration of ethyl alcohol, and thus it is understood that the amount of ethyl alcohol in the treated mice decreased quickly. Further, the present compound-treated mice were obviously quicker in recovery of intoxicated state, when observed visually. This indicates that by administration of the present compounds, the mice were stimulated in alcohol metabolic function of liver.

EXAMPLE 18—Effect on glucose metabolism:

Methods

The test compounds dissolved in olive oil and administered orally at the dose of 250 mg/kg to the mice. After 6 hours, 4.0 g/kg of glucose was orally administered. The same amount of glucose was given to the control animals. 0.02 ml of blood was taken from caudal vein of the mice at 30, 60, 90 and 120 min. after glucose administration. Blood sugar was measured by the procedure of Somogyi-Nelson. Number of animals used was 5 to 6 mice for each treatment.

Table 14

| Time (min.) | Results: Blood Sugar (mg/dl) | | | |
|---|---|---|---|---|
| | Control | Test Compounds Pre-treatment | | |
| | | Compd. 4 | Compd. 24 | Comp. 12 |
| 0 | 145±11.8 (100%) | 134±24.8 (100%) | 135±13.2 (100%) | 141±11.3 (100%) |
| 30 | 311±21.9 (214%) | 258±22.2 (192%) | 248±20.2 (184%) | 264±21.5 (187%) |
| 60 | 290±14.6 (200%) | 232±13.0 (173%) | 214±18.8 (158%) | 225±17.2 (160%) |
| 90 | 263±13.1 (181%) | 190±23.6 (142%) | 173±24.4 (128%) | 167±15.6 (118%) |
| 120 | 251±13.5 (173%) | 152±23.4 (113%) | 140±16.3 (104%) | 142±13.2 (100%) |

The blood sugar values of the each group showed peaks after 30 minutes, and no substantial difference was seen in the peak values. Thereafter, however, obvious difference was observed in the recovery of blood sugar value, and the present compound-treated groups were quicker in recovery. This indicates that by administration of the present compounds, the mice were stimulated in glucose metabolic function of liver.

What is claimed is:

1. A pharmaceutical composition for preventing liver necrosis, for preventing and curing hepatitis or fatty liver, for curing hepatocirrhosis, and for formation and excretion of bile flow or biliary salt, containing an effective amount sufficient for said purpose of a compound having the general formula,

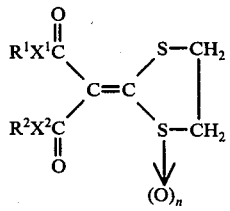

wherein $R^1$ and $R^2$, which may be the same or different, represent individually a $C_1$-$C_5$ alkyl group or a $C_1$-$C_4$ alkoxyethyl group; $X^1$ and $X^2$, which may be the same or different, represent individually an oxygen or sulfur atom; and $n$ is 1; and a pharmaceutically acceptable diluent.

2. A pharmaceutical composition according to claim 1, which contains the said compound in an amount of at least 0.01% by weight.

3. The composition of claim 1, wherein the said compound is 2-(diisopropoxycarbonyl)methyliden-1,3-dithiolan-1-oxide.

4. The composition of claim 1, wherein the compound is formulated into an administration unit form.

5. The composition of claim 4, wherein the administration unit form is any one of powder, granule, tablet, pill, sugar-coated tablet, capsule, ampoule, suppository, suspension, liquid, emulsion or injection.

6. The composition of claim 4, wherein the said compound is 2-(diisopropoxycarbonyl)methyliden-1,3-dithiolan-1-oxide.

7. A process for preventing liver necrosis, for preventing and curing hepatitis or fatty liver, for curing hepatocirrhosis and for formation and excretion of bile flow or biliary salt of animals including humans which comprises administering orally or parenterally to the animal an effective amount sufficient for said purpose of a compound having the general formula,

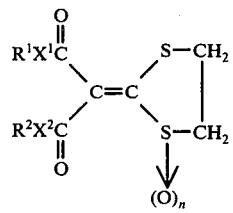

wherein $R^1$ and $R^2$, which may be the same or different, represent individually a $C_1$-$C_5$ alkyl group or a $C_1$-$C_4$ alkoxyethyl group; $X^1$ and $X^2$, which may be the same or different, represent individually an oxygen or sulphur atom; and $n$ represents 0 or 1.

8. The process of claim 7, wherein the administration is carried out parenterally.

9. The process of claim 8, wherein the dose is in the range from 0.01 to 250 mg. per kg. body weight per day.

10. The process of claim 7, wherein the administration is carried out orally.

11. The process of claim 10, wherein the dose is in the range from 0.1 to 500 mg. per kg. body weight per day.

12. The process of claim 7, wherein the compound is diethyl 1,3-dithiolan-2-ylidene malonate.

13. The process of claim 7, wherein the compound is ethyl isopropyl 1,3-dithiolan-2-ylidene malonate.

14. The process of claim 7, wherein the compound is diisopropyl 1,3-dithiolan-2-ylidene malonate.

15. The process of claim 7, wherein the compound is 2-(diisopropoxycarbonyl)methyliden-1,3-dithiolan-1-oxide.

16. The process of claim 7, wherein said necrosis, fatty liver, hepatitis or heptocirrhosis is induced by chemical poisoning.

17. The process of claim 16, wherein the chemical causing said poisoning is carbon tetrachloride, chloroform, bromobenzene, dimethyl-nitrosoamine, thioacetamide, allyl alcohol, D-Galactosamine, ethionine, a cadmium salt or a selenium salt.

18. The process of claim 7, wherein said liver necrosis, fatty liver, hepatitis or hepatocirrhosis has histopathological symptom similar to that induced by chemical poisoning.

19. A process for lowering the concentration of alcohol in the blood of animals including humans comprising administering orally or parenterally to the animal an effective amount sufficient for said purpose of a compound having the general formula,

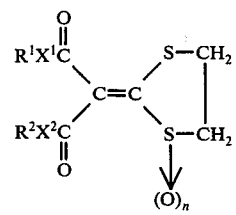

wherein $R^1$ and $R^2$, which may be the same or different, represent individually a $C_1$-$C_5$ alkyl group or a $C_1$-$C_4$ alkoxyethyl group, $X^1$ and $X^2$, which may be the same or different, represent individually an oxygen or sulphur atom; and $n$ represents 0 or 1.

20. The process of claim 19, wherein the compound is diethyl 1,3-dithiolan-2-ylidene malonate.

21. The process of claim 19, wherein the compound is ethyl isopropyl 1,3-dithiolan-2-ylidene malonate.

22. The process of claim 19, wherein the compound is diisopropyl 1,3-dithiolan-2-ylidene malonate.

23. The process of claim 19, wherein the compound is 2-(diisopropoxycarbonyl)methyliden-1,3-dithiolan-1-oxide.

24. A process for treating diabetes in animals including humans comprising administering orally or parenterally an effective blood-sugar depressant amount to said animal for stimulating the sugar metabolic function of the liver to lower the abnormally elevated concentration of sugar in the blood of a compound having the general formula,

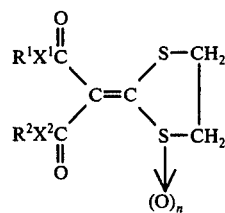

wherein $R^1$ and $R^2$, which may be the same or different, represent individually a $C_1$-$C_5$ alkyl group or a $C_1$-$C_4$ alkoxyethyl group; $X^1$ and $X^2$, which may be the same or different, represent individually an oxygen or sulphur atom; and $n$ represents 0 or 1.

25. The process of claim 24, wherein the compound is diethyl 1,3-dithiolan-2-ylidene malonate.

26. The process of claim 24, wherein the compound is ethyl isopropyl 1,3-dithiolan-2-ylidene malonate.

27. The process of claim 24, wherein the compound is diisopropyl 1,3-dithiolan-2-ylidene malonate.

28. The process of claim 24, wherein the compound is 2-(diisopropoxycarbonyl)methyliden-1,3-dithiolan-1-oxide.

* * * * *